US006941166B2

(12) United States Patent
MacAdam et al.

(10) Patent No.: US 6,941,166 B2
(45) Date of Patent: Sep. 6, 2005

(54) SOFTWARE CONTROLLED ELECTROPHYSIOLOGY DATA MANAGEMENT

(75) Inventors: David P. MacAdam, Millbury, MA (US); Stephen W. Sagon, Amherst, NH (US)

(73) Assignee: C.R. Bard, Inc., Murray Hill, NJ (US)

( * ) Notice: Subject to any disclaimer, the term of this patent is extended or adjusted under 35 U.S.C. 154(b) by 533 days.

(21) Appl. No.: 09/943,408

(22) Filed: Aug. 30, 2001

(65) Prior Publication Data

US 2002/0065459 A1 May 30, 2002

Related U.S. Application Data

(60) Provisional application No. 60/295,217, filed on Jun. 1, 2001, and provisional application No. 60/247,269, filed on Nov. 10, 2000.

(51) Int. Cl.[7] .............................................. A61B 5/04
(52) U.S. Cl. ..................................................... 600/521
(58) Field of Search ................................. 600/300, 508, 600/521, 523, 524; 607/9, 59; 345/440, 440.1, 502, 530, 536

(56) References Cited

U.S. PATENT DOCUMENTS

| 5,311,873 A | 5/1994 | Savard et al. ............... 128/696 |
| 5,848,972 A | 12/1998 | Triedman et al. ........... 600/508 |
| 6,599,242 B1 * | 7/2003 | Splett et al. ................ 600/300 |

* cited by examiner

Primary Examiner—George Manuel
(74) Attorney, Agent, or Firm—Darby & Darby (57) ABSTRACT

Methods for conducting an electrophysiology procedure using a programmed machine are described, including methods for managing discrete data capture requests received throughout the course of an electrophysiology procedure and for discretizing the display of independent data capture events that occur during the course of the electrophysiology procedure. These methods enable an operator to review location maps of sites visited during the course of a procedure and to review data from discrete moments in the procedure and to play back data over a sequence of times throughout the procedure, one moment at a time. The invention further includes software constructs that enable data management.

43 Claims, 5 Drawing Sheets

FIG. 1

EP SYSTEM

| SNAPSHOT SET | MEASURED VALUE | MEASUREMENT DATA |
|---|---|---|
| 1 ~122 | 2 ~124 | HR=80 ~126 |
| 1 | 0 | |
| 1 | -2 | |
| 1 | -4 | |
| 2 | -3 | HR=80 |
| 2 | 1 | |
| 2 | 1 | |
| 2 | 2 | |

120

PM SYSTEM

| SNAPSHOT | MEASURED LOCATION |
|---|---|
| 1 ~122 | $\{(X_1Y_1Z_1),(X_2Y_2Z_2),(X_3Y_3Z_3),(X_4Y_4Z_4)\}$ ~132 |
| 2 | $\{(X_1Y_1Z_1),(X_2Y_2Z_2),(X_3Y_3Z_3),(X_4Y_4Z_4)\}$ |

| SNAPSHOT | MEASURED LOCATION | MEASURED VALUE |
|---|---|---|
| 1 | $\{(X_1Y_1Z_1) \ldots \}$ | – |
| 2 | $\{(X_1Y_1Z_1) \ldots \}$ | $\{-3,1,1,2\}$ |
| 3 | $\{(X_1Y_1Z_1) \ldots \}$ | |

SOFTWARE CONTROLLED ELECTROPHYSIOLOGY DATA MANAGEMENT

This patent application claims the benefit of priority under 35 U.S.C. 119 from U.S. Provisional Application Ser. No. 60/247,269, filed Nov. 10, 2000, entitled "METHOD FOR VIEWING AND COMPARING ECG SIGNALS HAVING SUPERIMPOSED COMPLEXES" and from U.S. Provisional Application Ser. No. 60/295,217, filed Jun. 1, 2001, entitled "AN ALGORITHM TO MEASURE T-WAVE SUBTRACTION QUALITY," both of which are hereby incorporated by reference in their entireties.

FIELD OF THE INVENTION

This invention is directed to an apparatus and method for treating a cardiac arrhythmia such as ventricular tachycardia. More particularly, this invention is directed to improvements in electrophysiology (EP) procedures that permit data management across a number of measurements taken during the course of an electrophysiology procedure, including among other things, automated and a manually scripted review of procedure data under the control of software objects.

BACKGROUND OF THE INVENTION

Cardiac arrhythmias are a leading cause of death in the United States. The key to treating cardiac arrhythmias is to locate the target (active) site. A number of Catheter locating systems are known in the art, as exemplified by the following U.S. Patents:

U.S. Pat. No. 6,050,267, issued Apr. 18, 2000 and U.S. Pat. No. 5,944,022, issued Aug. 31, 1999, both entitled "Catheter positioning system" of inventors Nardella, et al.

U.S. Pat. No. 5,983,126, issued Nov. 9, 1999 and entitled Catheter location system and method, and U.S. Pat. No. 5,697,377, issued Dec. 16, 1997 and entitled Catheter mapping system and method," both of inventor Wittkampf.

U.S. Pat. No. 5,694,945 entitled "Apparatus and method for intrabody mapping;" U.S. Pat. No. 5,568,809 entitled "Apparatus and method for intrabody mapping;" U.S. Pat. No. 5,546,951 entitled "Method and apparatus for studying cardiac arrhythmias;" U.S. Pat. No. 5,480,422 entitled "Apparatus for treating cardiac arrhythmias;" U.S. Pat. No. 5,443,489 entitled "Apparatus and method for ablation;" U.S. Pat. No. 5,391,199 entitled "Apparatus and method for treating cardiac arrhythmias;" U.S. Pat. No. 5,713,946 entitled "Apparatus and method for intrabody mapping;" and U.S. Pat. No. 5,840,025 entitled "Apparatus and method for treating cardiac arrhythmias," all of inventor Ben-Haim, alone or with others, and all assigned to Biosense, Inc. of New Brunswick, N.J.

U.S. Pat. No. 6,226,543 of inventors Gilboa, et al., issued May 1, 2001 and entitled "System and method of recording and displaying in context of an image a location of at least one point-of-interest in a body during an intra-body medical procedure" and U.S. Pat. No. 6,188,355 of Gilboa, issued Feb. 13, 2001 for "Wireless six-degree-of-freedom locator."

U.S. Pat. No. 6,216,027 of inventors Willis, et al., issued Apr. 10, 2001 and entitled "System for electrode localization using ultrasound" and U.S. Pat. No. 5,820,568 of inventor Willis, issued Oct. 13, 1998 for "Apparatus and method for aiding in the positioning of a catheter," both assigned to Cardiac Pathways Corporation of Sunnyvale, Calif., and more generally referred to herein as the "Willis et al. patents."

The Willis et al. patents describe the use of ultrasonic sensors mounted on a mapping catheter and on two other catheters to determine the position of the mapping catheter by triangulation. The mapping catheter can include one or more electrodes suitable for ablation. By using triangulation techniques, catheters can be navigated through a patient with minimal use of fluoroscopy.

Also known in the art are electrophysiology (EP Systems) for recording and analyzing electrogram signals received from multiple electrodes, for example, from a multielectrode mapping and ablation catheter. The EP Lab System available from C.R. Bard, Inc., Murray Hill, N.J., for example, is able to automatically measure activation times on multiple channels simultaneously. Activation times are typically calculated relative to a stable recording channel such as a surface ECG.

Historically, EP Systems have provided a variety of physiological information to the operator without a true association of the location of the operative catheter at which the physiological information was measured. The physiological information conventionally obtained from a roving catheter includes, among other data, intracardiac ECG signals, temperature, pressure, and impedance.

One early attempt to mate physiological information of a heart with the location of a catheter called for the placement of a sensor-laden sack positioned about the heart. The sensors on the sock provided a position verses physiological-condition map on a display with a full color interpolated image of activation time, temperature, and other physiologic parameters. Placing the sock around the heart, however, was an invasive procedure.

A relatively modem approach proposed by Ben-Haim et al. combines a portion of an EP system with a catheter positioning system and joins the physiologic data together with location information into a data point. Multiple data points are gathered as the operator repositions a singular mapping catheter and records physiologic data at new catheter positions. The data points from these separate measurements are displayed together to define a map, although the data points are collected over multiple heartbeats and are limited to a single mapping electrode pair. Data from the separate measurements are also analyzed and the regions between them are interpolated and included in the map. The resulting map provides a view of changes of the physiologic parameter under investigation (e.g. activation time) with position.

For many procedures it is important to advise the operator of the locations that have already been examined. However, when a great number of locations have been examined, the physiological data associated with each of these locations can obscure meaningful data when all of this information is displayed together in a composite map as in prior art approaches. There remains a need in the art for the selective display of only a portion of the physiologic data that has been gathered. There also remains a need for a system and method that permits selective and sequential playback of data points selected in accordance with prescribed criteria. There further remains a need for a system and method that can sequentially display changes in physiologic parameters at a given set of locations before and after a procedure (e.g. activation time before and after ablation). There also exists a need to gather and display multiple measurements from a single heartbeat to increase the speed and accuracy at which data can be gathered. The present invention addresses these and other needs.

SUMMARY OF THE INVENTION

In one aspect, the present invention concerns a method for conducting an electrophysiology procedure using a programmed machine having a memory. The method includes the steps of displaying location data in a first window and physiologic data in a second window, freezing the first and second windows to a first moment in time during the electrophysiology procedure in response to operator action, disassociating in the memory of the programmed system any physiologic data from location data for any moment in time other than the first moment in time, and creating a set of data points for display in the first window. Each of the data points associates physiologic data at the first moment in time with location data at the first moment in time.

In another aspect of the present invention, there is a method for managing discrete data capture requests received throughout the course of an electrophysiology procedure. This method includes the steps of obtaining physiologic data from sites adjacent one or more locations of a catheter distal tip portion, obtaining location data concerning a location of each of the sites, providing an index value in response to a request, at any given point in time, to capture these data, associating in first and second memories the obtained physiologic data and the obtained location data, respectively, with the index value, and updating the index value prior to further data capture.

In a preferred embodiment, the foregoing method for managing discrete data capture requests includes the further step of creating a set of data points, the data points associating the physiologic data in the first memory with the location data in the second memory for any one of the given points in time. In a particularly preferred embodiment, the data points are displayed in a first window, and the first window can also display a map of the locations visited during the course of the electrophysiology procedure.

In a related aspect of the invention, another method for managing discrete data capture requests received throughout the course of an electrophysiology procedure is disclosed. That method includes the steps of obtaining physiologic data from sites adjacent one or more locations of a catheter distal tip portion, obtaining location data concerning a location of each of said sites, providing an index value in response to a request, at any given point in time, to capture these data, associating in first and second memories the obtained physiologic and the obtained location data, respectively, with the index value, updating the index value prior to repeating further data capture, and displaying in a first window a map of the locations visited during the course of the electrophysiology procedure using the obtained location data for a plurality of index values.

According to yet a further aspect of the invention, a method for managing discrete data capture requests received throughout the course of an electrophysiology procedure is disclosed. In response to a user request to capture data at any given point in time during the course of the electrophysiology procedure, the method first associates in a first memory an index value with physiologic data obtained from sites adjacent one or more locations of a catheter distal tip portion at the given point in time and associates in a second memory the index value with location data obtained concerning a location of each of the sites at the given point in time. The index value is then utilized to associate in a memory segment of a programmed system the physiologic data in the first memory with the location data in the second memory. A set of data points is created for display in a first window using the information in the memory segment and displayed in the first window. Then, the physiologic data is disassociated from the location data in the memory segment for any index value other than the utilized index value whereby the set of data points displayed in the first window show physiologic data for only one particular point in time during the course of the electrophysiology procedure at any moment.

According to still another aspect of the present invention, a method for discretizing the display of independent data capture events that occur during the course of an electrophysiology procedure is described. That method includes the steps of utilizing an index value to associate in a memory segment of the programmed system physiologic data in a first memory with location data in a second memory, creating a set of data points for display in a first window using the information in the memory segment, displaying the set of data points in the first window, and disassociating the physiologic data from the location data in the memory segment for any index value other than the utilized index value, whereby the set of data points displayed in the first window show physiologic data for only one particular point in time during the course of the electrophysiology procedure at any moment.

In a particularly preferred implementation of any of the foregoing methods, the first window comprises one or more panes each of which can have a user-selectable tab to activate a given pane. Only one of the panes need by activated at a time, and the panes can have a transparent background to permit viewing of underlying panes, or an opaque background to obscure from view any underlying pane. The index value can be selected by the user via the user-selectable tab, or by selecting from a location map a location that was visited or a set of locations that were visited. A sequence of physiologic data that was captured during the course of the electrophysiology procedure can then be retrieved and displayed. The index value that is used to retrieve physiologic data also can be selected by a program executing in the programmed system so as to satisfy at least one predetermined criterion such as an earliest activation time.

The foregoing and other aspects, features and advantages of the invention can be appreciated from the attached Drawings and Detailed Description of an Illustrative Embodiment.

DETAILED DESCRIPTION OF AN ILLUSTRATIVE EMBODIMENT

By way of overview and introduction, the present invention concerns improvements in electrophysiology (EP) procedures including new systems and methods that permit discrete management of multiple physiologic data measurements that are taken during the course of an electrophysiology procedure. In particular, the invention provides data management across a number of measurements that are part of a common electrophysiology procedure, including among other things, automated and a manually scripted review of procedure data under the control of software objects.

In the illustrative embodiment, the invention is implemented via a programmed system which includes controlled data transfer between an existing EP system that may be within an procedure room such as the Bard EP LabSystem available from C.R. Bard, Inc., Murray Hill, N.J., and a real-time position management (PM) system such as the real-time position monitoring system (RPM) made available by Cardiac Pathways, Inc., Sunnyvale, Calif. The Bard EP Labsystem and Cardiac Pathways RPM system preferably each have respective memories and processors that can be programmed to implement the functionality described herein. It should be understood, however, that the invention can be implemented by combining the EP and PM systems into a unitary system, with the core functionality of each retained. Thus, the term "system" as used in this specification includes stand-alone machines with a communication link therebetween as well as "sub-systems" of a single, unitary machine that performs the EP and PM functions described herein.

The EP system records and analyzes electrogram signals from multiple catheter electrodes. Typically, one or more catheters are used in conducting an electrophysiology procedure, and at least one of the catheters supports an element for obtaining physiologic data from sites adjacent a location of a catheter distal tip portion. Most typically, the catheter supports a number of electrodes, each obtaining data from sites adjacent respective locations of the catheter distal tip portion, but other elements can be provided on or within the catheter to obtain particular physiologic data such as a thermistor which is used to gather temperature data or a transducer which can be used to gather pressure data. The EP system is also capable of automatically measuring activation times on multiple channels simultaneously. The activation times are typically calculated relative to a stable recording channel such as a surface ECG, which is also part of the EP system.

Illustratively, a roving catheter is used together with two reference catheters with the location of each catheter being ascertained using ultrasound signals and triangulation techniques, as described in the aforementioned Willis et al. patents. The ultrasound elements are preferably positioned along a distal tip portion of a catheter, at prescribed intervals. The ultrasound elements are positioned proximate to electrodes of a mapping and/or ablation catheter, or proximate to other sensors such as pressure transducers, thermocouples, and various devices conventionally included along a working portion of a catheter to acquire local information of interest. Thus, a variety of sensors can be used to obtain local information that is being managed by the system described herein. In alternative embodiments, the catheter distal tip portion can be provided with a transmitter for transmitting signals to a receiver outside of the patient, or can be provided with a receiver that receives signals from an external antenna.

Alternatively, again, a plurality of electrodes can be used for obtaining physiologic data and the same structure (namely, the electrodes) can be used to transfer signals between the electrodes and external transmitters or receivers. Together with data processing the transferred signals permit location data of the electrodes to be obtained. Such signals are described in the aforementioned Wittkampf and Nardella patents.

The PM analyzes the position of three catheters relative to each other using catheter-mounted ultrasonic sensors and a method of triangulation described in the aforementioned Willis et al. patents. Two of the catheters are nominally denoted as reference catheters and the third a mapping/ablation catheter, though any of the three catheters can be used for mapping and/or ablating functions. Each of the catheters typically has multiple ultrasonic sensors and multiple electrodes (or other elements for obtaining physiologic data) to supply local physiologic information to several channels of the EP System. One benefit of using the PM system is that the catheters can be navigated with minimal use of fluoroscopy, though other navigation systems can be used such as the systems disclosed in patents to Super Dimension, Inc., Nardella, Wittkampf, and others, as well as other techniques such as real-time imaging. However, the use of ultrasonic sensors works well, and these sensors can be used to obtain location data concerning the location of whatever element is supported on the catheter for obtaining physiologic data. For example, an ultrasonic sensor can be positioned a fixed and known distance between two electrodes, and so multiple means for obtaining physiologic data can be associated with a single position sensor. Thus, it should be understood that there is no need for one-to-one correspondence between the number of physiologic sensors and the number of position sensors, and, as noted above, these sensors can be one and the same depending on the technique employed to determine position. The location of the position sensor along the catheter is not a primary concern, rather, what is important is that the location of the physiologic sensor can be determined reliably.

One type of catheter conventionally used to gather physiologic data is a multielectrode mapping and/or ablation catheter that permits measurement of local information from a series of closely spaced electrodes supported on the same device. This local information is gathered all at once in a single measurement or "snapshot," and provides measured values of a particular physiologic parameter, either directly from the electrode (e.g., a potential) or after processing (e.g., determining an activation time). Depending on the type of physiologic data to be displayed, it may undergo processing prior to a value (or color or other indicator) being displayed. The snapshot is taken in response to a request to capture data, which is typically a request made by the operator although the request can be taken automatically in response to a program. An index or identifier is associated with the snapshot, for example a number or a time stamp, and the index is updated with each snapshot request.

The local information thus includes a set of measured values that is conventionally recorded by and stored in a first memory included in an EP system, and is associated with the snapshot (e.g., an index). A great number of snapshots are taken during the course of a typical electrophysiology procedure, with each snapshot occurring at a location or set of locations known from the locating means of the catheter(s). The location data for each snapshot is preferably stored in a second memory included in the PM system, and is also associated with the snapshot index. The association of a snapshot with physiologic data on the one hand and with location data on the other hand can be made in response to the request to capture data, with an index value provided automatically for use with each snapshot. The index value is updated for each snapshot so that data captured at any moment in time during the course of the electrophysiology procedure can be managed.

Not all of the data from these discrete measurements is of relevance to the operator. In part, this is because the snapshots are taken at different times in the electrophysiolgy procedure, and, in this regard, it should be recognized that the operator has the ability to repeat a snapshot at a specific location, for example, to compare activation changes at the same location over a period of time such as before and after tissue ablation. Data gathered before the ablation may have no relevance apart from this comparison and so a map that combines all gathered data into a single map might provide a distorted view of the prevailing conditions of the organ under treatment.

Known systems do not permit segregation of measurement data into manageable portions, or controlled data display across multiple measurements. Rather, known systems combine each successive measurement into a single map, or combine data from multiple measurements to create sufficient points to create a map in a single, active display. In the preferred embodiment, however, discrete data management is enabled by storing each measurement as a separate snapshot for display to the user, and by permitting physiologic and location data from one or more snapshots to be associated with one another in accordance with a user- or program-defined set.

A. Snapshots

As noted above, a "snapshot" is a discrete measurement taken during the course of an electrophysiology procedure. A number snapshots are taken during the course of the procedure in response to operator action at a user interface, and each one is associated with the capture of physiologic data, such as activation times, voltage measurements and correlation maps (e.g., maps that result from template matching and T-wave subtraction as described in the aforementioned provisional patent applications that are incorporated herein by reference) at a particular point in the procedure. The user interface includes a number of screen objects that instigate the data capture process, both with regard to the local information that has just been measured and with regard to the location of the electrode at which the local information was measured.

Preferably, the display of the PM system includes a first window in which a location map of all locations visited during the course of the electrophysiology procedure is displayed. These locations can be for a plurality of snapshots. The locations are displayed, preferably using a neutral indicator such as a grey color marker, for each of the snapshots. Meanwhile, the EP system manages all of the local information that is captured and governs its distribution to the PM system. The local information is displayed in a second window, which can be an active pane on the same display as the first window of the PM system.

At any given moment in the procedure, however, the operator may wish to see the value of the local information obtained for a given location or set of locations concerning a given snapshot. The local information can be displayed as a map segment in the location map at the location(s) at which that snapshot was taken by creating a set of data points for display in the first window. Each data point associates physiologic data stored in the first memory with location data stored in the second memory for any one point in time during the course of the electrophysiology procedure. Alternatively, the association of physiologic data with location data can be made in a memory segment that is part of either of the first or second memories or a separate memory segment. The data points are preferably created by retrieving either the physiologic data from the first memory or the location data from the second memory using the index value as the search criterion. Thus, the snapshot number or a time stamp value is used to access portions of the memories and retrieve data associated with that snapshot, so that the set of data points displayed in the first window includes physiologic data that was captured at one particular point in time during the course of the electrophysiology procedure. Preferably, the display of the EP system is synchronized to the point in time that corresponds to the active snapshot, as described below.

Preferably, management of discrete data capture requests in accordance with the preferred embodiment includes disassociating physiologic data from location data for a given snapshot prior to associating physiologic data with location data for a different snapshot. This can be done by purging data from the memory that maintains the association, or by updating a property of a data object, for example, the MeasuredValue property of the Location object described below.

The relevant software objects that can be used to create a snapshot are Freeze, SaveSnapshot and SendData and are described in the next section.

Figure 1:
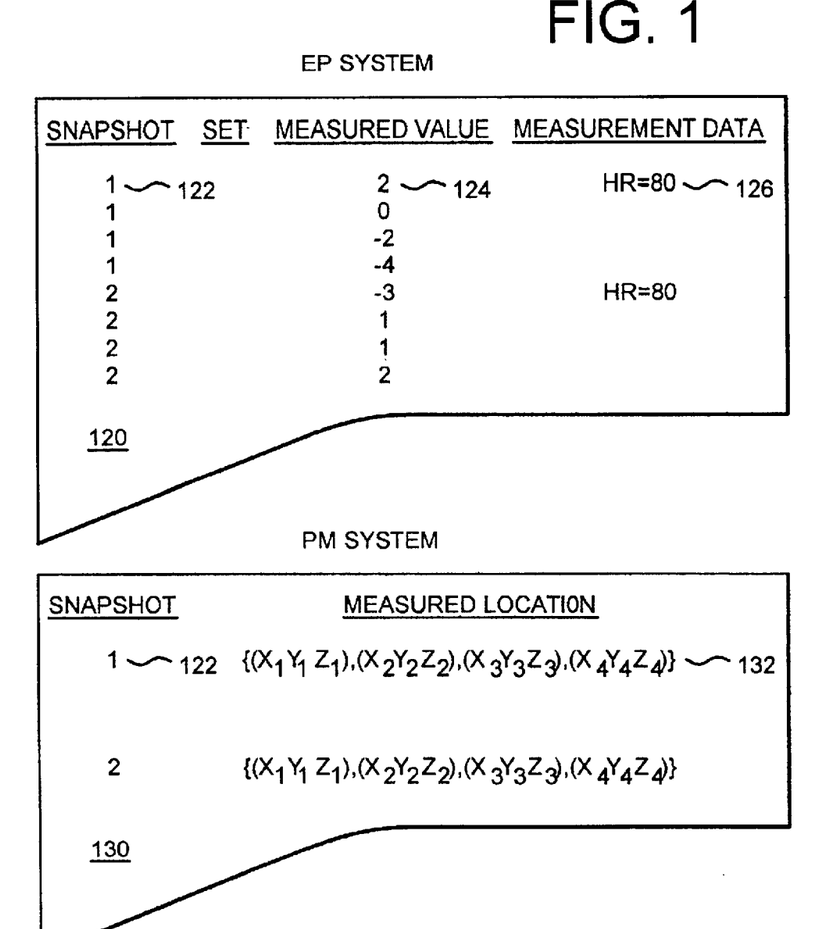
FIG. 1 illustrates portions of the memories of the EP system and position management (PM) system.

As shown in FIG. 1, the EP system logs into a memory 120 the following measurement data:

1. Log: snapshot number 122, procedure time, or other index.
2. Log: local information 124 obtained by each electrode (MeasuredValue(y)) such as activation time, potentials, correlation between a reference beat and a current heart beat.
3. Not logged: location information 132 for any electrode.
4. Log: measurement data 126, that is, data common to all electrodes when a measurement was taken such as the patient's heart rate, the fiducial reference point, blood pressure and other vitals such as pulse oximetry, and any comments entered by the operator.

Measurements taken at the catheter (e.g., potentials) are provided directly from the catheter to the EP system. Notably, the EP system does not log the location 132 of any electrode, which information is not necessary to perform an EP analysis of the measured data. On the other hand, the PM system logs into a memory 130 only the following data 1. Log: snapshot number 122, procedure time, or other index.
2. Not logged: any local information 124 obtained by an electrode.
3. Log: location information 132 (e.g., X, Y, Z coordinates) for each Electrode(y) ("MeasuredLocation(y)").
4. Not logged: any measurement data 126 or parameter associated with the patient.

It should be noted that the PM system does not ever log any local information 124 obtained by any electrode from any snapshot. In a combined system, the memories 120, 130 can be portions of a contiguous memory bank, as well as the memory segment 140.

Figure 1A:
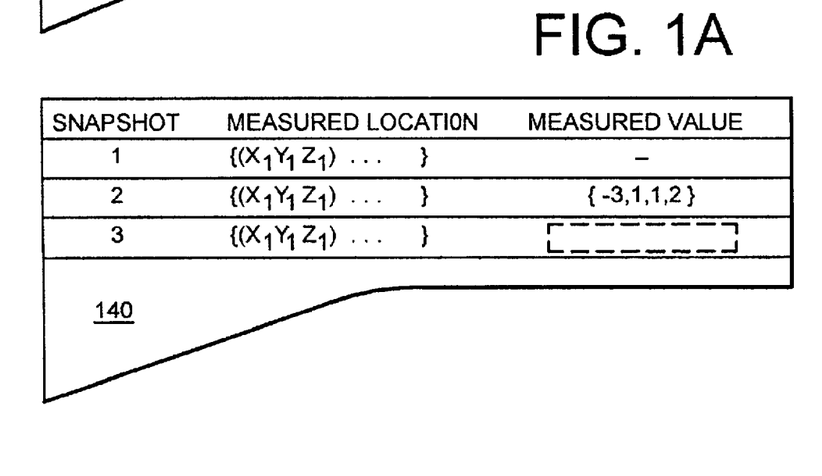
FIG. 1A illustrates a different portion of the memory of the PM system containing measured values from a single snapshot.
Figure 6:
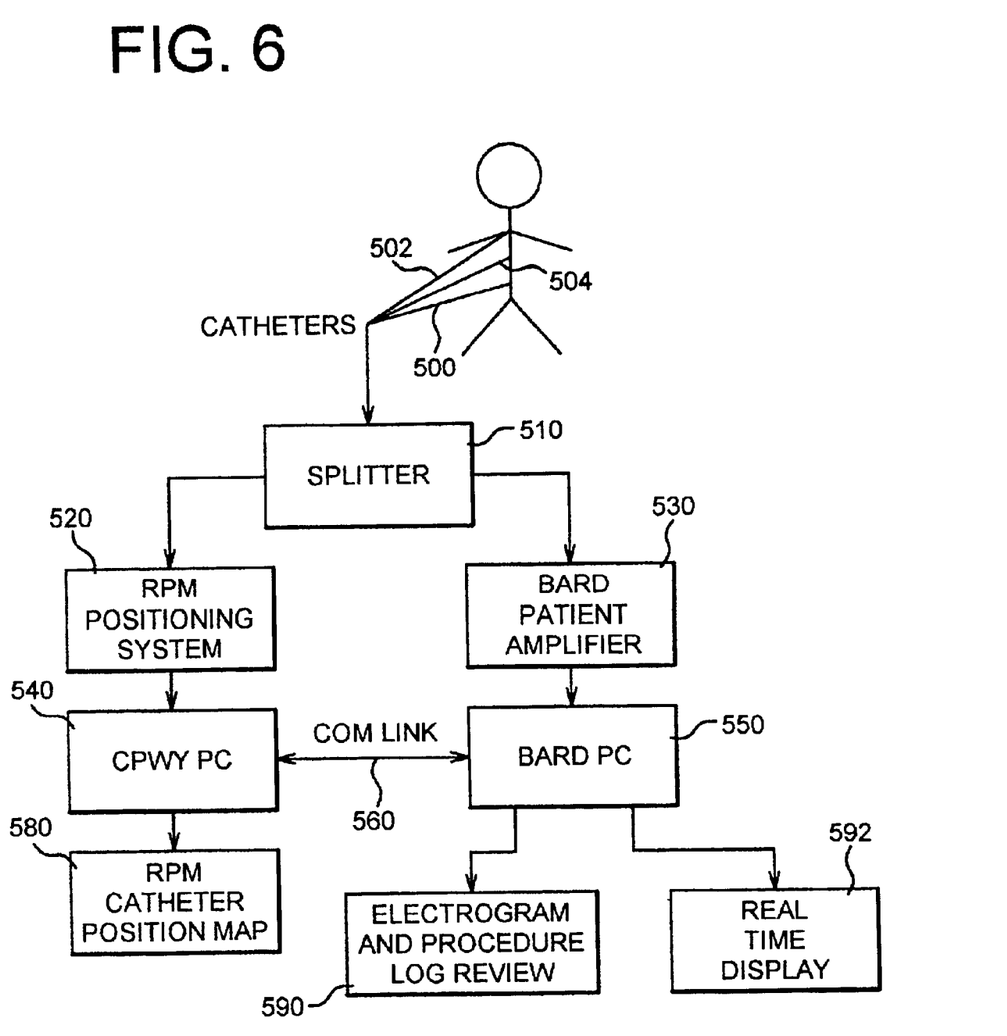
FIG. 6 is a systems block diagram of an embodiment that utilizes a particular position management system.

The snapshot number, procedure time, or other reference (generally denoted index 122) can be provided by the EP system, the PM system, or engrafted to the data by the splitter (see FIG. 6). Preferably this index 122 is provided by the EP system as an index value. The EP system also supplies the PM system with a limited amount of local information to display at any one time. In the preferred embodiment, the EP system only provides local information captured from one or more electrodes from a single snapshot. In a more preferred embodiment, the PM system confirms to the EP system that all local information has been purged prior to receiving local information concerning a different snapshot. FIG. 1A illustrates this preferred arrangement.

As shown in FIG. 1A, the PM system includes both measured location data (X, Y, Z) and measured value data (e.g., activation time ("AT")) in its memory segment 140 for snapshot 2. These two data segments are coordinated through the snapshot number for display as a "data point" of the form (X, Y, Z, LocalParameter), for example, (X, Y, Z, AT). If the operator were to inspect the activation time from a different snapshot, say, snapshot 1, then in the preferred embodiment the data in the measured value column or cell is purged prior to receiving further information from the EP system. The memory segment 140 need only store measured value data and an index 122 to permit coordination with measured location data and the display of data points.

The data contained in the PM system log (memory 130) is preferably displayed in a multi-dimensional display (that is, a perspective view) showing the locations of each electrode on the catheter. Any snapshot that is not matched with local information in the memory segment 140 preferably has the electrodes indicated as a neutral colored dot or marker. On the other hand, any local information included in memory segment 140 is preferably depicted in a color selected to represent the value of the physiologic parameter under review, or the value is indicated adjacent the marker. For example, if the measured value concerns activation time, then the value of the data can be correlated to a color which indicates earlier or later activation times on a relative or absolute scale. Alternatively, the computed activation time value provided to the PM system by the EP system can be displayed on or alongside the marker.

Figure 2:
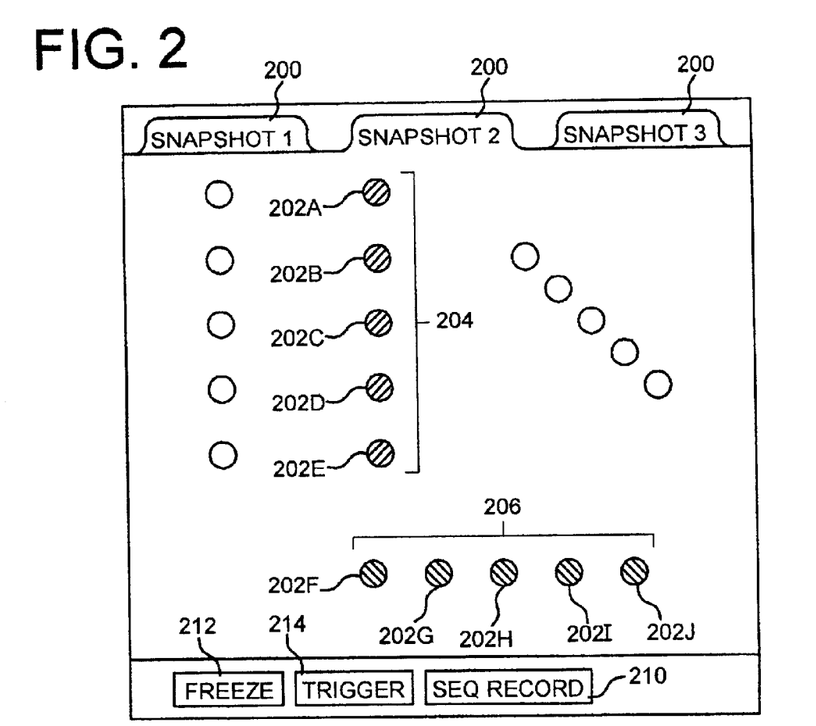
FIG. 2 illustrates a plurality of snapshots taken during the course of an electrophysiology procedure, overlaid upon one another with transparent backgrounds.

With reference to FIG. 2, multielectrode catheters 204 and 206 have been placed within a patient and the coordinate locations of electrodes 202A–202J supported on those catheters are displayed as a series of overlapping snapshots. (Each of these catheters is illustrated as having five electrodes 202A–E and 202F–J, though any number of electrodes can be provided and, in fact, the data of FIGS. 1 and 1A illustrate data collected from catheters having only four electrodes.) Each snapshot is preferably included in its own pane within the first window of the PM system. The snapshots depict a roving catheter 204 and a single reference catheter 206. In practice, a second reference catheter would be used but has been omitted from the diagram for clarity. Each snapshot preferably includes a tab 200 that can be selected by the operator to bring the snapshot to the foreground and cause local information to be displayed.

A user can select a tab 200 to thereby select an index value and activate a given pane. The user also can select an index value in other ways, such as by selecting from the location map one or more locations that were visited, which causes physiologic data to be retrieved (e.g., from the first memory) using the index value(s) associated with the selected location(s).

Only one snapshot can be in the foreground at any given moment, and so only one pane is active at a time, though the user can select which of the panes is to be active at any given time. In FIG. 2 snapshot 2 is in the foreground, and so the "data points" for that snapshot are shown. That is to say, both location information and local information are combined into a data point and displayed on the PM system, but only the information gathered at the time that snapshot 2 was taken. As for snapshots 1 and 3, only location information is shown and so a large portion of the display is a location map illustrating to the operator the locations of prior measurements.

In FIG. 2, the snapshots are represented in panes with transparent backgrounds so that they can be overlaid upon one another while permitting the operator to see what other locations have been examined. More specifically, FIG. 2 illustrates that the reference catheter 206 was in the same location in each of the three depicted snapshots, and that the roving catheter 204 was moved about from snapshot to snapshot. Data points are shown for snapshot 2, whereas only neutral colored markers are provided to indicate the locations of the electrodes of the roving catheter 204 at the time that snapshots 1 and 3 were taken.

Figure 3:
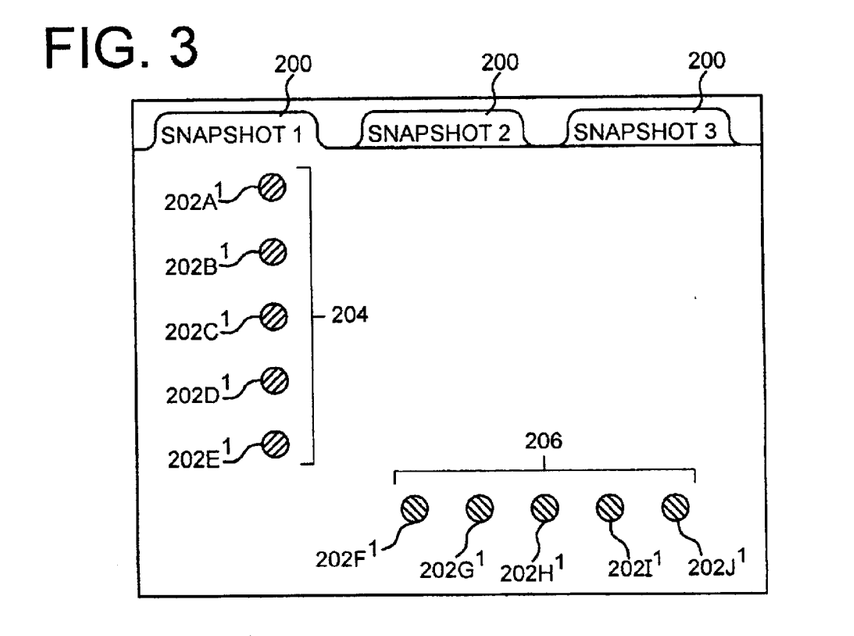
FIG. 3 illustrates the plurality of snapshots of FIG. 2, in which the snapshots now have opaque backgrounds.

In FIG. 3, the snapshots are represented in panes with opaque backgrounds, permitting only one measurement to be visible to the operator at a time (namely, the measurement in the top layer pane). The local information associated with one or all of the electrodes 202A'–202J' can be displayed for that snapshot. FIG. 3 displays the data points associated with snapshot 1, rather than snapshot 2, because the tab for snapshot 1 has been selected (e.g., by a conventional left-click selection of a mouse) which caused that snapshot to appear in the foreground.

A snapshot can be hidden or deleted from view by right-clicking on the Tab 200 and selecting the desired action from a pop-up menu (e.g., hide, un-hide, delete, print, publish to . . . ).

Instead of a series of overlays, snapshots can be combined into a single display window which shows all of the catheter locations for which local information has been saved. This arrangement is similar to that illustrated in FIG. 2, except there are no tabs. Even in this arrangement, however, data points need only be displayed for a single snapshot at a time.

B. Data Review

The preferred embodiment permits discrete display of multiple, independent data capture events that may occur during the course of an electrophysiology procedure. The operator can review such data in a variety of ways. For instance, electrogram signals can be reviewed on the EP system, and if the operator sees local information of interest (which is associated with a particular electrode), he or she can issue a SendData command which will cause a data point to be created on the PM system for that electrode, or for all of the electrodes in the snapshot containing the local information of interest. This can be repeated for multiple electrograms. Likewise, the operator can select one or more locations depicted in the three-dimensional PM location map as prior measurement sites, and RequestData commands will issue to the EP System to recall the local information corresponding to the selected electrodes (or group of electrodes) for each snapshot that the operator selects. Preferably, the EP system display is synchronized to show all physiologic data (for example, electrograms and markers) recorded at that point in time.

Data points from non-active snapshots are neutralized by purging local information from the memory segment 140 of the PM system whenever a different snapshot's data points are to be reviewed. The purging step is accompanied by neutralizing the displayed data point (e.g., converting a color to gray or eliminating the display of a value of the local information).

C. User- and Program-Defined Scripts

A salient feature of the preferred embodiment is the ability to initiate sequenced review of data, either through scripts defined by the user or by a program within the EP system. Sets of electrograms or locations that were previously measured can be selected by the operator, or culled from data in accordance with sort and filtration algorithms to identify locations and local information of interest. The set of points and their order in the sequence provides a script that initiates an automated playback of gathered data, which playback can be played at a user-settable speed and continuously looped, if desired. The visual effect is that of a virtual map constructed in the operator's mind by flashing data from discrete and isolated measurements in a newly defined sequence. If the snapshots are provided in stacked layers having transparent backgrounds, then the visual effect is that data points are created and destroyed in a sequence defined by the script, with data points from only one snapshot ever existing at any given moment.

Scripts therefore permit an operator or user to cycle through data garnered from discrete physiologic data measurements. Scripts can be used to identify pathological trends through movie-like presentation of the physiologic data that was acquired over the course of the procedure. Any variations in the acquired data from one location to a nearby location can be correlated with measurement data (e.g., heart rate) to better understand the variations. Also, scripts can be used for training new users.

1. Manually Defined Scripts

Figure 4:
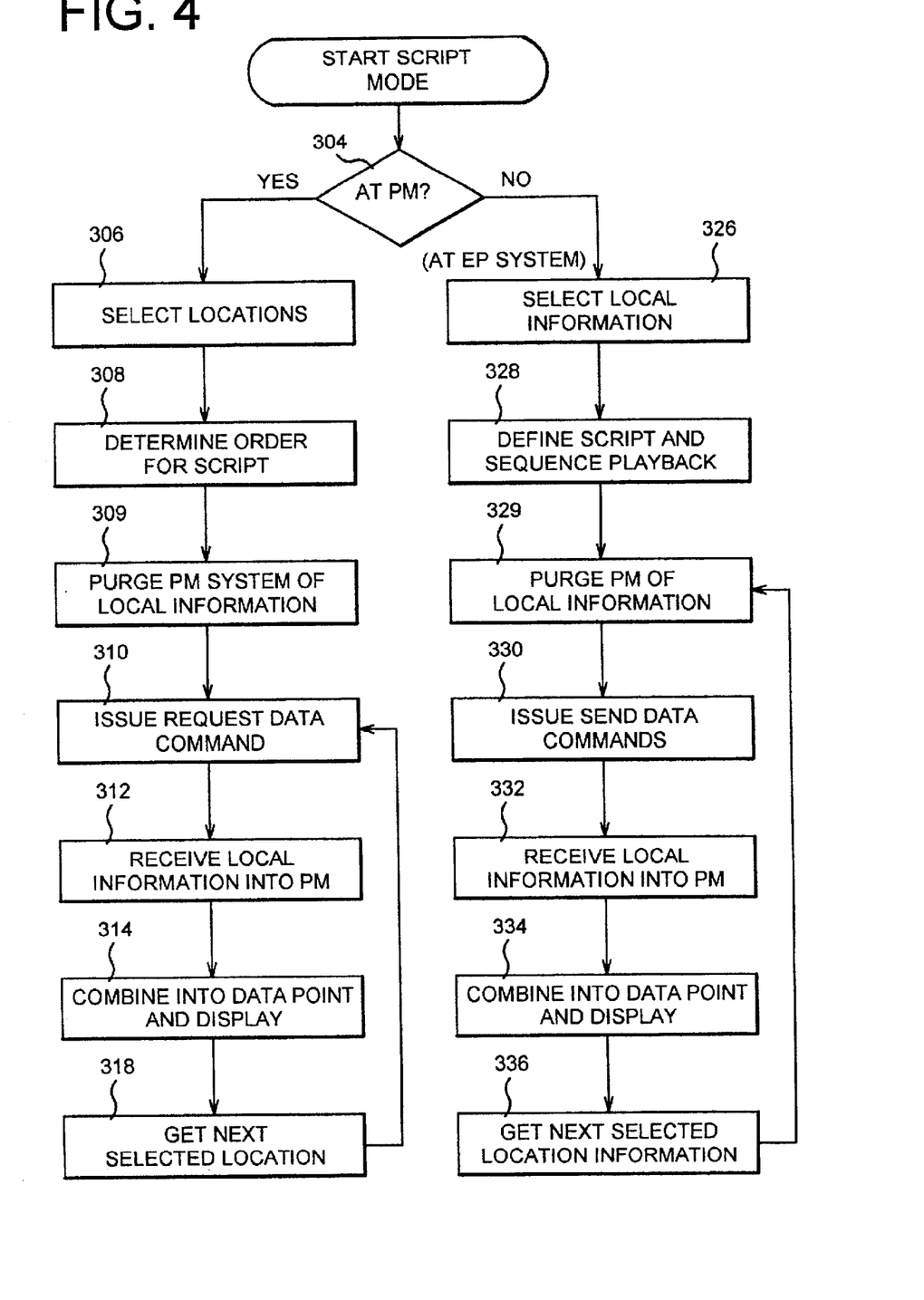
FIG. 4 is a flow chart illustrating the handling of user-defined scripts.

With reference now to FIG. 4, the operator defines a script and initiates sequence playback at the PM system by first selecting a sequence record mode. This can be achieved by activating a suitable control such as button 210 shown in FIG. 2. If the sequence record mode was selected, for example, by an onclick event handler associated with the button 210, a test is made at step 304 to determine whether the script is being defined at the PM (in terms of locations) or at the EP system (in terms of local information). A sequence is defined at the PM system by the operator manually selecting a series of locations that were visited using a mouse or other input device, or by selecting a region of positions by a drag operation or the like. This is done at step 306, and the selections are preferably stored. The order of selection (or the direction of the drag operation) can be used to determine the sequence for playback, which is determined at step 308.

After purging any local information contained in the memory segment 140, as shown at step 309, the script causes the PM system to issue a RequestData command to the EP system, at step 310, to send measured values for each location identified in the script, in the determined sequence. The EP system responds with a SendData command, and the PM receives local information for a given snapshot at step 312 which is stored in the memory segment 140 and sequentially retrieves the physiologic data for each selected location in the set of locations. The local information is combined with the location information for the selected electrode in a manner described more fully below, and displayed on the PM at step 314. A next selected location (or the first selected location in a continuous loop) is retrieved at step 318 and then the process loops back to step 309 to display a further data point until interrupted. Consequently, prior to issuing a subsequent RequestData command, the local information is ordinarily purged from the memory segment 140 in the PM system (either because it concerns a different snapshot or because the PM system is configured to always purge data prior to requesting data) at step 309, leaving only location information for the prior selected location. If the request concerns the same snapshot, the local information need not be purged. In any event, the script is executed and data points are created and destroyed under automated control. The playback speed can be adjusted to suit the operator's needs (e.g., by right-clicking the SEQ RECORD button 210. The process flow can continue in a loop indefinitely, repeatedly retrieving the data referenced in the script, or the process flow can execute one cycle such that the data in the script is only retrieved once.

On the other hand, if the sequence record mode was initiated at the EP system, as determined at step 304, then the script is defined by the operator by selecting a number of electrograms (or other local information) that was recorded by the EP system and included in its data log (see FIG. 1). A sequence is defined at the EP system by the operator manually selecting a series of log entries or data directly from the EP system display (i.e., electrograms, activation times and other local information), as indicated at sep 326. This is done using a mouse or other input device. The order of selection defines the sequence for playback, as indicated at step 328. Preferably, the EP system precedes each SendData command with a Purge command which causes the PM to purge its memory segment 140 prior to receiving further local information, as indicated at step 329.

The script then causes the EP system to issue a SendData command to the PM system, at step 330, to send local information associated with an electrode from a given snapshot. The PM system then receives local information at step 332, combines it with the location information for the selected electrode as described below and displays a data point on the PM at step 334. A next local information data (or a pointer thereto) is obtained from the script and retrieved at step 336, and the process loops back to step 329 to display a further data point on the PM system. As before, the script is executed and data points are created and destroyed under automated control, with the speed of playback being adjustable at the operator's discretion.

2. EP System Program Scripts

A sequence of data points can be selected by a program executing in the programmed system preferably, the EP system) and played back to the operator instead of being selected in response by the operator from the raw procedure data. The program can automatically select physiologic data to be retrieved in accordance with one or more predetermined criteria. For, example, a sorting algorithm can be initiated on the basis of activation time or some other measurement or calculation that has been made to present the operator with information in a manner which is unlikely to correlate with the sequence that the snapshots were taken, or other readily observable pattern. Local information also can be sorted by snapshot number, procedure time, or some other time stamp or reference to play back the information garnered during the course of the procedure at a prescribed rate. Operators can select the sort criterion through the EP system interface, for example, electing to display data points in sequence from shortest to longest activation time, from best correlation to worst, or to display only a portion of that sorted data. Physiologic data to be retrieved and displayed to the operator can be selecting after the sorting step. Instead of sorting the physiologic data, a subset of the physiologic data can be defined, for example, as a result of a filtering step, and data selected/sorted from the subset.

As with manual scripts, local information is conveyed to the PM system for one snapshot at a time, preferably after the PM system has purged local information for any other snapshot. If information for only one electrode among a group of electrodes is to be displayed, then the electrode is also identified in the data transmission. The local information provided by the EP system is correlated at the PM system with a particular electrode in the specified snapshot and a data point is created on the display of the PM system, in the same way as described above. Each data point is neutralized by purging the local information from the PM system before further local information concerning a different snapshot is provided to the PM system.

C. Software Objects

The preferred embodiment can be implemented through a user interface driven by a number of software modules or objects that include methods to permit communication among the objects and, through a data link, communication between an electrophysiology (EP) system and a real-time position monitoring (RPM) system. The preferred embodiment utilizes software objects in an object oriented program environment to enable rapid development of a number of electrophysiology software applications; however, applications can be constructed from software modules and routines, as understood by those of skill in the art. The objects of the preferred embodiment enable management of the measured values from a number of snapshots. These objects are discussed below.

1. LocalParameter Object

Objects concerning local parameters are members of a class called Measurement. The Measurement class provides for measurement of particular physiologic parameters including but not limited to activation time, electrogram potential, tissue impedance, and tissue temperature as well as information derived from any obtained physiologic parameter(s). Preferably, for each physiologic parameter to be measured, a different object is instantiated from the Measurement class. For example, the objects can be instantiated to have the following form:

LocalParameter (Snapshot(x), MeasuredValue(y))

Preferably, the LocalParameter object has properties that are set to hold measurement data. The Snapshot property takes a value that represents the present measurement. Its value, x, can be set by an index that is incremented with each measurement taken, by a procedure time, or in accordance with some other reference. The MeasuredValue property takes values that are obtained from a given electrode y. If the catheter is a multielectrode catheter, then the MeasuredValue property contains a one by y array of values. Other objects can inspect the MeasuredValue property of the LocalParameter object in connection with data display, and local information processing (e.g., sorting activation times to locate an earliest time, or a sequence of times from earliest to a later time). When a unipolar or bipolar electrode catheter is used in a procedure to obtain local information, the parameter y is not needed.

As an illustration, the LocalParameter object can be local electrical activation time ("activation time"), a measurement of the time elapsed from a common reference time event of the cardiac cycle to a fiducial point during the electrical systole. The activation time measured at a given electrode represents a unit of local information that can be used to construct an activation map data point at a single location when combined with the location of the electrode at the time of measurement. The activation time at a given location can also be used in a data filtered map, in accordance with the present invention, to guide an operator's review of a large amount of measurement data.

The ActivationTime object is an instance of the Measurement class mirroring the general case described above for the LocalParameter object, and the same properties, namely:

ActivationTime (Snapshot(x), MeasuredValue(y))

2. Location Object

This object is an instance of a Location class and is used to hold location information concerning the location of one or more electrodes at a given point in time, defined by the Snapshot property. There need be only one object declared from this class, but the class definition permits other objects to be created that extend the functionality of the Location object (by inheritance). Snapshot property, as described above, accepts a value that represents the present measurement, e.g., an index x that is incremented with each measurement, or a procedure time, or some other reference.

The Location object can be instantiated as follows:

Location (Snapshot(x), MeasuredLocation(y), MeasuredValue(z))

The MeasuredLocation property contains coordinate data of the location of a given electrode y at the time of the snapshot, or information that can be resolved into coordinate data (such as potentials that are comparable to potentials from reference catheters to triangulate a location as in the aforementioned Willis et al. patents). If the catheter is a multielectrode catheter, then the MeasuredLocation property contains an array of information with entries for each electrode y. The MeasuredValue property can hold the value of a physiologic parameter obtained for the current snapshot under review by the operator (e.g., the last snapshot taken or one being examined in response to a script or other operator action). For all other snapshots, the property value can be set to "null," e.g., by a purging method of another object or module. Other objects can inspect the MeasuredLocation property in connection with data display and processing (e.g., sequencing locations to study changes in a physiologic parameter from one location to another). When a unipolar or bipolar electrode catheter is used in a procedure to obtain local information, the argument y is not needed.

3. Freeze Object

Throughout a procedure, the EP System continuously acquires electrogram (and other) information in real-time and displays that information to the user. The local information is supplied by the electrodes supported on the indwelling catheters. Concurrently, the PM system continuously acquires the electrode position and displays in real-time any movement of the catheter. The PM system also receives from the EP system local information for a given snapshot and displays this information on the PM display. More particularly, local information associated with a particular electrode in a given snapshot is displayed at the corresponding position calculated by the PM system for that electrode. Local information from different snapshots, i.e., those occurring at different points in time, are not stored by the PM system and are never displayed together by the PM system. By isolating the data from a given measurement or snapshot, the software of the preferred embodiment departs from traditional approaches which have sought to construct into a single physiologic map data that has been captured at different points in time.

At any given moment during the course of the procedure, the operator may desire to freeze the display in order to review the acquired information and obtain an analysis of the data (e.g., activation time data on one or more data channels). A Freeze object is provided for this purpose and is activated by selecting a suitable control such as the button 212 shown in FIG. 2. (Upon pressing the freeze button, its caption property is toggled to Save Snapshot, as discussed below.) The Bard EP LabSystem available from C.R. Bard, Inc., Murray Hill, N.J., displays activation times for each channel relative to a reference channel, and automatically annotates the display with calculated activation times relative to the current position of a user-settable marker while the display is frozen. The Freeze object of the preferred embodiment, when activated by the user at the EP system, extends this capability by causing data to be temporarily logged in the PM system as well as the EP system.

The Freeze object includes EPLogData and RPMLogData methods that cause the EP system and PM system to respectively log the data shown in FIG. 1. The Freeze object further includes a Snapshot property that identifies the particular measurement being logged, and can be denoted Freeze (Snapshot(x))

In response to selection of the Freeze object, the EP system sends a message to the PM system to include a unique identifier of the snapshot (e.g., the snapshot number, the procedure time corresponding to the time that the user requested to freeze the display, or some other indexed variable), and the coordinates of each electrode. The PM system logs this information into its memory. For example, The PM system can create a bookmark to store the position of each of the electrodes (including electrodes on reference catheters, if used) at that moment in time. The PM system displays the location information for that moment in time in the first window. The PM system also displays in the first window the local information obtained by the electrodes in the current snapshot for that same moment in time, but not together with local information obtained from any other point in time or snapshot. Optionally, the second window, that is, the active pane displayed on the EP system is also frozen to the moment in time when the freeze object was selected.

The operator can review the activation times on the frozen display of the EP system and manually make any modifications as desired, for example, the operator can move a marker on the electrograms to a different location. The operator also can turn off markers on channels that are not of interest. The effect of these changes is to recalculate activation times, and the new values are displayed on both the EP system and the PM system, due to revised data being sent to the PM system over the data link between these two systems.

Other data is managed by the EP system and the PM system, including SetNumber data, a variable which is settable by the user or by another object to group multiple MeasuredValue data/MeasuredLocation data from one or more snapshots into a common set. SetNumber data is described below.

4. SaveSnapshot

SaveSnapshot is a method of the Freeze object, *CONFIRM and is operator-activated by pressing the Save Snapshot button, which appears in place of the Freeze button 212 after the freeze button has been pressed. If the operator does not wish to save the temporarily logged snapshot, he or she can press the trigger button 214 to resume real-time data display.

The SaveSnapshot method is utilized after the operator has configured the electrogram markers as desired. The measured values (e.g., activation times) are then saved to the memory 120 of the EP system along with any measurement data and together with a snapshot number, procedure time or other time stamp, or some other index or reference. The SaveSnapshot method also causes the PM system to save into its memory 130 the catheter positions at that snapshot. The data saved is the local information and location information at the moment that the Freeze button 212 was pressed.

5. NewSet

This object contains the location information or local information that is selected for inclusion in a script, the snapshot from which that information came, the electrode involved in gathering that information, and the order for sequential playback. NewSet can also include user preferences that override default property values such as playback speed.

NewSet associates selected information from one or more snapshots together. A SetNumber variable can be included in the memory of the EP system or the PM system to facilitate script playback by associating the data together with a common searchable parameter. SetNumber can be an integer or an integer array (if the same data is to be included in multiple sets). NewSet can be maintained at either the EP system or the PM system.

6. RecallSet

The only parameter for the RecallSet object is a set number. RecallSet causes the PM system to display all of the locations included in a specified set, without displaying local information. Its form is:

RecallSet (q)

7. Trigger

This object resumes real-time data capture when the Trigger button 214 is pressed. It discards frozen data (location and local information) that was reserved in case the SaveSnapshot method were invoked.

8. SendData

The SendData object operates within the EP system and causes local information for a particular electrode and snapshot to be sent from the EP system to the PM system. It is sometimes issued in response to a RequestData object, described below, and other times is used to initiate an unrequested data transfer. In connection with an unrequested data transfer, SendData can be preceded by Purge, described below. Its form is:

SendData (Snapshot(x), Elecrode(y), MeasuredValue(y))

9. RequestData

This object operates within the PM system and communicates with and receives data from the EP system.

RequestData (Snapshot(x), Elecrode(y), MeasuredLocation(y))

10. Purge

The Purge object includes a method that purges the memory segment 140 of the PM system. This object permits the EP system to control data transmission to the PM system and limit the local information resident in the PM system to data concerning a single snapshot.

Additional objects and methods can be defined to implement applications for management of multiple physiologic data measurements that are taken during the course of an electrophysiology procedure. For example, manual changes to a marker position at the EP system will cause a recalculation in activation time and can instigate without further user intervention a revision of the data in the logs of the EP system. If that snapshot is being displayed on the PM system, revised local information can be dispatched for display to the user, in synchronization with the settings made at the EP system. As another example, deletion of a snapshot at either system can cause a deletion in the log of the other system. As can be appreciated from the foregoing, the use of software objects permit flexible and rapid development of electrophysiologic systems.

Figure 5:
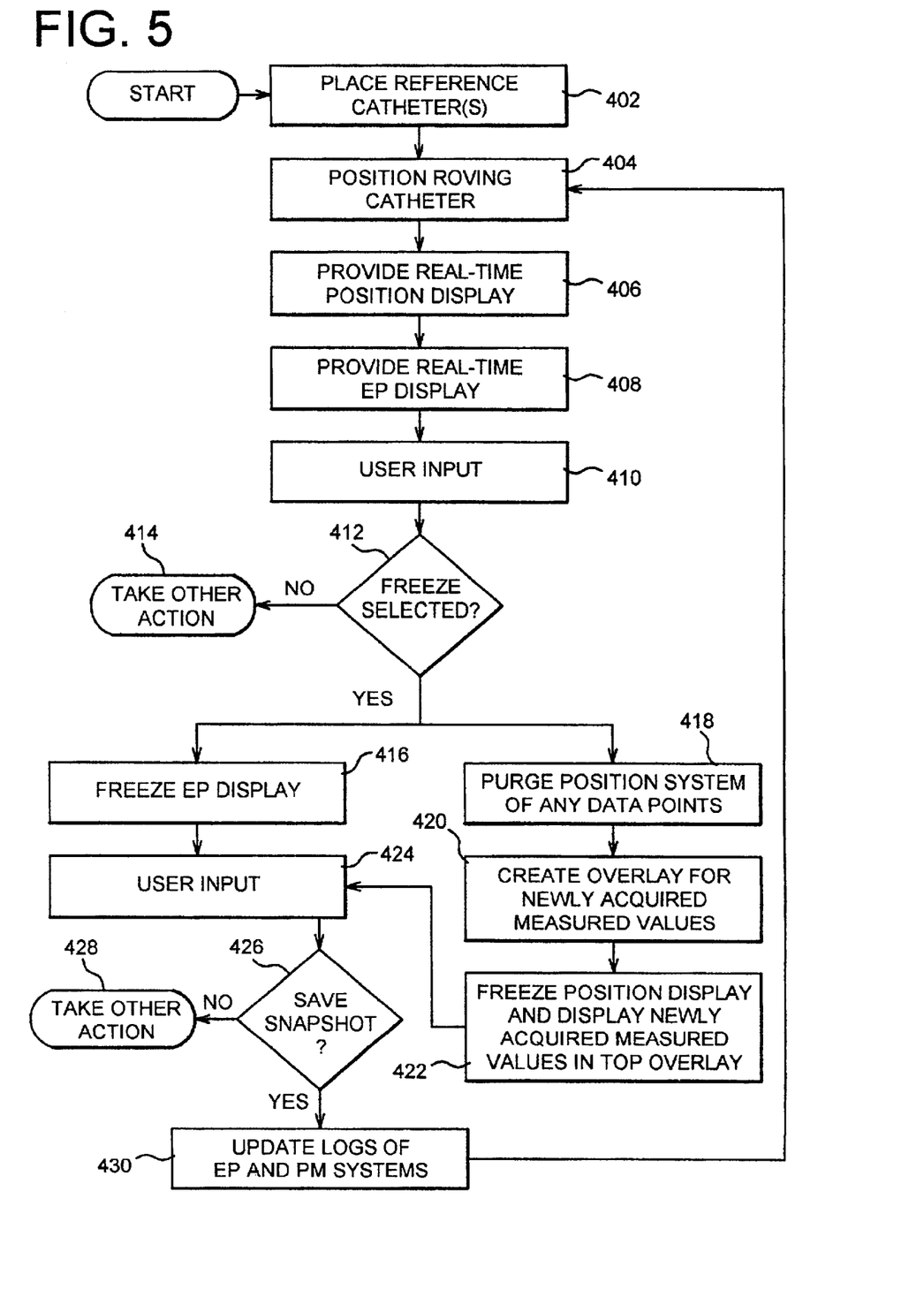
FIG. 5 is a flow chart illustrating an electrophysiology procedure conducted in accordance with the preferred method.

We reference now to FIG. 5, an electrophysiology procedure conducted in accordance with the preferred embodiment is described. The procedure begins with the operator placing references on or within (e.g., catheters) the patient. The preferred position system utilizes ultrasonic sensors and triangulation methods to locate a roving catheter within the patient. At step 402, two reference catheters are preferably placed within the patient, in the vicinity of the region of interest (e.g., a heart). At step 404, a roving catheter is advanced through the patient until its distal tip portion is positioned at a site adjacent to or within an organ or other bodily structure. The PM system meanwhile provides a real-time display of the movement of the catheter, as indicated at step 406. Concomitantly, the EP system provides a real-time display of signals gathered at one or more electrodes or other devices supported on the roving (and reference) catheters, as indicated at step 408.

Once the catheters have been suitably placed and positioned, the operator can utilize one or more controls provided at the user interface. User input is received at step 410 and tested, among other reasons, to see whether the freeze button 210 was selected. This test, made at step 412, will freeze the displays of the EP system and the PM system, and cause other actions to be taken by the two systems. If the freeze button had not been pressed, then another action is taken, as indicated at step 414.

On the other hand, if the freeze button was selected, as was tested at step 412, then several processes proceed in parallel. First, the EP system display is frozen, as indicated at step 416. Second, any data points (that is, coordinated locations and measured values of local information) are purged from the PM system, at step 418. Also, an overlay is created in the preferred embodiment for displaying newly acquired measured values at the time of the freeze button 212 was pressed. This happens at step 420. At step 422, the position of the roving catheter is frozen on the PM system display and the measured values managed by the EP system are provided to the PM system and displayed in the newly created overlay. The user has the opportunity to save or discard the data and the input is received from the user at 424. A test is made to determine whether the user has indicated if he or she wishes to save the snapshot, as tested at step 426. If not, then some other action is taken at step 428. Otherwise, if the user does wish to save the snapshot then at step 430 the logs of both the EP and the PM systems are updated and the system loops back to permit the re-positioning of the roving catheter and to provide real-time displays on the EP and PM systems.

FIG. 6 is a system block diagram illustrating a preferred arrangement in which signals from indwelling catheters 500, 502, 504 are split at a split of 510 into location signals which are provided exclusively to a position management system such as the Cardiac Pathways RPM system 520 and local information signals that are produced exclusively to the EP system 530. Each of the systems 520, 530 in the presently preferred embodiment is associated with a respective computer 540, 550 and a communication link 560 between the computers 540, 550 permitting controlled and limited transfer of local information signals from the EP systems to the RPM system. It should be understood that the EP and RPM systems can be implemented on a single computer. Each system 540, 550 outputs data to a display 580, 590, respectively. The RPM system outputs location information as well as some local information under control of the EP system 550, and the EP system outputs only local information. The EP system also provides a display of procedure data concerning multiple, prior measurements on the display 590, e.g., in a window 592.

The roving catheter as well as any reference catheters can be portrayed in real-time within a heart chamber. A basic image of the heart can be obtained, if desired, using a transesophageal echocardiograph or other means for imaging the patient's anatomy. Such imaging can acquire multiplane images of the heart chambers prior to commencing the EP procedure (e.g., a mapping study) to permit 3-D reconstruction of the chamber. Typically, the acquired image is gated or synchronized to a fiducial point in time during the cardiac cycle using a timing signal, for example, an end-diastole signal. A sample and hold circuit responds to the timing signal by sampling the signals from the transesophageal catheter and reconstructs a three-dimensional image of the heart chambers that indicates the endocardial morphology. In addition, the image can portray the location of the roving and reference catheters within the heart; however, catheter location is preferably determined independent of any basic image.

Once the catheter distal tip portion has been located, the located position can be converted into electrical image signals that can be superimposed on a heart chamber image disclosing wall architecture acquired by the same sensors, or other means of imaging. The catheter image and the heart chamber image are combined in a proper three-dimensional correspondence using the location information provided by the roving and reference catheters. U.S. Pat. No. 5,694,945 of Ben-Haim et al. describes one such process. In this regard, the PM system optionally includes an image processor or module that permits images of the heart chambers to be acquired from available imaging modalities (e.g., fluoroscopy, echo, MRI, etc.). The image is acquired with sufficient projections (e.g., bi-plane fluoroscopy, several longitudinal or transverse cross-sections of echocardiography) to be able to perform 3-dimensional reconstructions of the cardiac chambers' morphology. Images can be acquired at specific times during the ablation procedure. In one mode, the basic image is recorded at the beginning of the procedure to allow determination of the cardiac chamber anatomy and the positions of reference catheters in the heart. This image can be used as a basic source of information to describe the heart chamber morphology. In another mode, the image used is instead a 3-D model of the organ and is retrieved from a data store and can be edited or modified to conform to the patient. The image processor can identify (i) the location of chamber boundaries using the methods of edge enhancement and edge detection, (ii) the dynamics of chamber morphology as a function of the cardiac cycle; and, if coupled to a catheter location processor, (iii) catheter locations relative to the chamber boundaries. By analyzing the displacement of the catheter tips during the cardiac cycle the image processor can calculate the regional contractile performance of the heart at a given moment during a procedure. This information can be used to monitor systolic contractile functions before and after the ablation procedure, if desired.

It is also necessary that the heart chamber architecture does not displace or deform during the treatment. To correct for displacement of the heart chamber that occurs during the cardiac cycle the catheter location is sampled at a single fiducial point during the cardiac cycle. To correct for displacement of the heart chamber that may occur because of breathing or patient movement, the reference catheters are placed at specific points in the heart chamber during the mapping procedures.

At each mapping stage of a typical electrophysiology procedure, namely, during sinus rhythm mapping, pace mapping and focal arrhythmia mapping, the EP system preferably determines the local activation time relative to a common fiducial point in time. The EP system can perform one or more of the following signal processing functions:

2.A. Origin Site Determination

Determine the most likely origin site of the patient's arrhythmia based upon the body surface ECG recordings during focal arrhythmia. The most likely focal arrhythmia origin site will be detected by analyzing the axis and bundle morphology of the ECG, and by using the current knowledge of correlation between focal arrhythmia morphology and focal arrhythmia origin site.

2.B. Sinus Rhythm Mapping

2.B.1 Delayed Potential Mapping

Using intracardiac electrograms recorded from the mapping catheter tip during sinus rhythm the EP processor will detect and then measure the time of occurrence of delayed diastolic potentials. Detection of late diastolic activity either by (1) ECG signal crossing a threshold value during diastole; by (2) modelling the electrical activity at a user-defined normal site and then comparing the modelled signal with the actual signal, and estimating the residual from the normal activity; by (3) using a band pass filter and searching for specific organized high-frequency activities present during diastole; or by (4) using cross-correlation and error function to identify the temporal position of a user-defined delayed potential template. This analysis will be performed on a beat-by-beat basis, and its results will be available to the next stage of data processing and referred to as the time of delayed potential occurrence.

2.C. Pace Mapping

2.C.1 Correlation Map

In a "pace mapping mode" the ECG processor will acquire ECG data while the patient's heart is paced by an external source at a rate similar to the patient's arrhythmia cycle length. The ECG data will be acquired from the body surface electrograms, and the signal will be stored as a segment of ECG with a length of several cycles. The signal acquired will then be subjected to automatic comparison with the patient's own focal arrhythmia signal. The comparison between arrhythmia morphology and paced morphology will be performed in two stages: First, the phase shift between the template focal arrhythmia signal and the paced ECG morphology would be estimated using minimal error or maximal cross-correlation for two signals. Then, using this phase shift estimated from an index ECG channel, the similarity of the focal arrhythmia and the paced ECG morphology will be measured as the average of the cross-correlation or the square error of the two signals of all channels recorded. This two-stage calculation will be repeated each time using a different ECG channel as the index channel for determining the phase shift. At the end of this procedure the minimal error or the maximal cross-correlation found will be reported to the operator as a cross-correlation value (ACI) of this pacing site.

2.C.2. Local Latency

The ECG processor will measure the pacing stimulus to ventricular activation. The earliest ventricular activation will be measured from the earliest zero crossing time of the first derivative signal generated from each of the body surface ECG recordings acquired while pacing. This interval will be reported to the operator and will be later used in the process of judging the suitability of the site for ablation.

2.D. Focal Arrhythmia Mapping

2.D.1 Pre-potential Map

During spontaneous or induced focal arrhythmia the ECG processor will search for a pre-potential present on the mapping/ablation electrode electrogram. The potential will be marked either automatically (by a threshold crossing method, by band pass filtering, or by modelling normal diastolic interval and subtracting the template from the actual diastolic interval recordings) or manually by the user-defined fiducial point on the pre-potential signal. The processor will measure the interval between the time of the pre-potential (PP) signal and that of the earliest ventricular (V) activation as recorded from the body surface signals, and the interval will be calculated and reported to the user. The ECG processor will report on a beat-by-beat basis the value of the PP-V interval.

2.D.2 Premature Stimuli Local Latency

During focal arrhythmia, when premature extra stimuli will be delivered to the mapping catheter, the ECG processor will detect the time of a single premature signal delivered to the mapping/ablation catheter and the earliest local activation (judged by the presence of non-diastolic activity following a predetermined interval at the mapping/ablation catheter and the presence of a different signal morphology shape and value at the body surface electrograms when compared to their value at one cycle length before that event). The presence of electrical activity on the mapping/ablation electrode and the presence of an altered shape of the body surface morphology will be termed as a captured beat. In the presence of a captured beat the ECG processor will calculate the intervals between the stimulus and the preceding earliest ventricular activation (termed V-S) and the interval between the stimulus and the following earliest activation of the ventricle (termed S-V'). The ECG processor will report these intervals to the user after each extrastimulus delivered. Also, the intervals V-S and S-V' will be graphically plotted as a function describing their dependence. The ECG processor will update the plot after each extrastimulus.

2.D.3 Phase Shifting of Focal Arrhythmia by Premature Stimuli

The ECG processor will identify the effects of the extrastimulus on the phase shifting of the focal arrhythmia as recorded by body surface electrograms. A user-defined body surfaced channel electrogram of non-paced focal arrhythmia morphology will be used as a template (segment length equal to twice focal arrhythmia cycle length), and the electrogram of the same channel acquired for the same duration following the delivery of an extrastimulus during focal arrhythmia will be used as a test segment. The ECG analyzer will compare the template and the test signal morphologies (using minimal error function or maximal cross correlation) to assure that the focal arrhythmia was not terminated or altered. If focal arrhythmia persists, the ECG analyzer will calculate the phase shift caused by the extrastimulus. Phase shift will be calculated as a part of the focal arrhythmia cycle length needed to be added or subtracted to regularize the focal arrhythmia time series.

2.D.4 Focal Arrhythmia Termination by Premature Stimuli

The ECG processor will look for a non-capture event following the extrastimulus. In that event the ECG processor will look for alteration in the focal arrhythmia following the extrastimulus delivered. If the focal arrhythmia was terminated (as defined by returning to normal ECG morphology and rate), a note of non-capture termination will be generated by the ECG processor. In case there was no capture but focal arrhythmia morphology did not change, the operator will be notified to change the coupling interval for the coming extra stimuli.

2.E. Focal Arrhythmia Mapping

Mapping can be used to locate focal arrhythmias in the atria as well as the ventricles. Pace Mapping with the ECG is conventionally used to detect the origin of VT. It may also be used to locate the site of atrial tachycardias especially with the aid of computerized methods to objectively and efficiently perform real time pace mapping. One of the difficulties inherent in pace mapping in the atria is small size of the focal P-wave during a premature ectopic beat (termed PAC). The small P-wave is oftentimes obscured by the ventricular signal, most notably the T-wave. Computerized techniques can be used to process an incoming electrical signal representing heart activity to display a derived P-wave without any overlap with a preceding T-wave during a PAC. See the aforementioned U.S. provisional applications that were incorporated herein by reference.

2.E.1 Template Matching/Pace Mapping of Focal Arrhythmias

Any recorded ECG waveform can be used as a reference to compare to another recorded ECG waveform or to a real time ECG waveform. The comparison is performed in a two step process where first a reference template is selected by the user to describe the beginning and end of an ECG waveform segment to be used as a comparison template. Next the user selects the region of data to be used for comparison—either from pre-recorded data or from the real time data stream. Software comparisons are used to find the best match against the reference template over the region specified, or in the case of real-time analysis, to find the best match updated over a defined period of time, for example every second. The criteria for "best match" utilizes a correlation coefficient calculation across all twelve leads of the ECG and finds the best alignment. A visual display showing the aligned reference beat (template) overlayed on the beat undergoing analysis give the user feedback as to the closeness of the match. A correlation coefficient calculated for each ECG lead gives a quantitative indicator of the match. A composite average is also calculated and is displayed in a unique color enhanced bar graph indicator which is especially useful when real time template matching is being performed.

Template matching may be used to compare two spontaneous beats or it can be used to pace map, i.e., to compare a paced beat to a spontaneous beat. A Region of Interest (ROI) indictor can be manipulated by the user to exclude certain portions of the waveform from analysis. This is useful during pace mapping where pacing artifacts on the surface leads can be excluded from the region of analysis. The ROI indicator can also be used to specify a preference for T-wave or P-wave matching as they are oftentimes morphologically very similar.

2.E.2 T-Wave Subtraction

An ECG having an overlapping P and T wave is processed to remove the T-wave and thereby display the P-wave without any overlap, so that a clinician may observe the P-wave when performing their diagnosis of the heart.

In general, according to the method, the QRS-T in sinus rhythm is selected as a template. This template is subtracted from the QRS-T-P' signal in the PAC to be studied yielding the P-wave. The QRS-T signal used as the template may be from a single beat or it may be derived from an average of multiple beats. The QRS-T signal (or average) used as the template is selected so that the preceding QRS-QRS interval is equal (or nearly equal) to the QRS-QRS interval immediately preceding the QRS-T-P' signal to be studied.

The QRS complex is used as a means to synchronize and align the QRS-T template and the PAC beat for subtraction. The alignment is automated by the algorithm for the best match based on the composite correlation coefficient across the 12 Lead ECG. The practitioner has the option of shifting the template match left or right on a sample by sample basis with the resulting composite correlation coefficient updated at each new position.

Different display views showing the derived P-wave, alone, or overlayed with the original PAC beat or reference template are available as an aid to the practitioner.

P-waves that have been derived using the T-wave subtraction method can be signal processed further to remove unwanted artifacts caused by respiration or noise.

2.E.3. Template Matching of Derived P-Waves

Once a derived P-wave has been identified from the tachycardia or premature atrial beat (PAC), it can be compared to a previously captured reference template.

3a. More specifically, one or more spontaneous P-waves may be identified using the subtraction method described above and compared with one another using a correlation waveform analysis. This can be used to determine if the spontaneous P-waves have the same focal origin. This can be done in real time or in review from previously recorded data.

3b. In addition, one or more derived spontaneous P-waves can be identified and compared to a library of P-waves of known focal origin to predict the most likely site of origin.

3c. In addition, once a derived spontaneous P-wave is identified by the T-wave subtraction method as described above and in the aforementioned U.S. provisional applications, then the practitioner can begin atrial pace mapping following the template matching/pace mapping method also described above. A roving pace mapping catheter is maneuvered within the atria (or adjacent vessels such as the pulmonary veins) until the derived paced P-wave is nearly identical to the derived spontaneous P-wave. This comparison of derived P-waves may be done on pre-recorded data or in real time.

To generalize, two or more waveforms X, Y, . . . , may form a composite waveform (e.g., ECG waveform with P on T complex) that due to timing and amplitude relationships causes the individual waveforms to be obscured or hidden. If a singular, unadulterated sub-component waveform (e.g. X or Y) can be identified, and if it has similar timing characteristics that allow it to be synchronized with the composite waveform, then it can be subtracted from the composite waveform to derive the other sub-component waveform(s). Sub-component waveforms, either derived, native state, or pace induced, can be quantitatively compared to one another using correlation analysis. This analysis may be done in real time.

The invention permits streamed data playback of discretized moments in time to show data that can be presented in the following time-blended maps maps joining measured or derived values with location information:

(1) Spatial location of the endocardium;

(2) Sinus rhythm activation map (isochronous map);

(3) Diastolic potential occurrence time isochronal map for sinus rhythm mapping;

(4) Correlation map for pace mapping;

(5) Local latency isochronal map during pace mapping;

(6) Activation time isochronal map during focal arrhythmia; and (7) Pre-potential isochronal map during focal arrhythmia mapping.

(8) Focal arrhythmia mapping including T wave subtraction.

The output device will use a computer screen or a holographic imaging unit that can be updated on a beat-by-beat basis. The output will include the following information: superimposed on the basic image the position of the catheter will be represented as a symbol on the ventricular wall. The maps will be plotted and overlaid on the same image.

The distal tip portion of the catheter is preferably localized in the manner described in the aforementioned Willis et al. patents using information sensed from the roving catheter and at least two reference catheters.

Electrical activation acquired at the mapping and/or ablation catheter distal tip portion is analyzed by an electrophysiologic signal processor within the EP system. The local electrogram, after being filtered, is analyzed in a conventional manner to detect the local activation. For example, activation time can be detected using amplitude or slope measurement techniques, by template fitting, or by manual notation by the user. The interval elapsed from previous end-diastole to the present local activation is the local activation time (AT). The association of the location of the sensor with the activation time generates a single data point as can be found in a conventional, non time-discretized, activation map. The activation times AT for each site can be presented using a color code or a cross-correlation index. Also, the color coding can represent the duration of the local electrograms, the presence of fragmented activity as well as various other variables calculated by the electrophysiologic processor.

Body surface ECG acquired is analyzed in the electrophysiologic signal processor of the EP system according to a pace mapping algorithm. The association of the location of the pacing electrode with the cross-correlation index (ACI) of that site yields a single data point as can be found in a conventional, non time-discretized, pace map.

The signals from the sensor electrode (59) are supplied to an electrophysiologic signal processor (60) which calculates the local activation time delay by subtracting the absolute local activation time from the absolute reference time measured from the body surface electrogram (61) of the present heart cycle.

If pacing poles are provided on the indwelling catheters, they can be connected to a pacemaker source which activates the heart starting at the site of contact of the heart and the pacing poles. Simultaneously acquired ECG is saved and processed in the electrophysiologic signal processor. Cross-correlation analysis is carried out in the signal processor, and the resulting cross-correlation index (ACI) is transferred to the display unit and associated with the location of the catheter tip to be superimposed on the image of the heart chamber at the appropriate location.

The algorithm used to calculate the cross-correlation index while pace mapping. Body surface ECG data is acquired at two stages. First, during spontaneous or pacing induced focal arrhythmia, and second during pacing the endocardium at different sites. The ECG data acquired during focal arrhythmia are signal averaged, and a template is constructed (T.sub.ch, for each channel recorded). During endocardial pacing the ECG data is acquired, and the same number of beats (N) is acquired to calculate the signal averaged QRS (P.sub.ch, for each channel recorded). The algorithm then calculates the phase shift between P.sub.ch and T.sub.ch, which yields for the first channel the maximal cross-correlation. This time shift is used to shift the remaining channels and calculate for them the cross-correlation. All cross-correlations for all channels are summarized and stored. The algorithm then uses the next channel recorded to calculate the time shift that will cause maximal cross-correlation in this channel. Now this time shift is applied for all cross-correlations between P.sub.ch and T.sub.ch, and again all cross-correlations are summarized. This procedure is repeated for all channels, and the maximal cross-correlation achieved is used as the value of the cross-correlation of the T.sub.ch and the P.sub.ch at this site on the endocardium.

Ablation can be performed using radiofrequency energy, laser, cryotherapy, microwave, D.C. energy or the like.

The above principles can be applied for mapping other structures of the body, for example, of the urinary bladder, brain, or gastrointestinal tract. Dependent upon the examination technique, the catheter may be replaced by a needle whose tip portion includes the locatable sensor port.

Although modifications and changes may be suggested by those skilled in the art, it is the intention of the inventor to embody within the patent warranted hereon all changes and modifications as reasonably and properly come within the scope of their contribution to the art.

We claim:

1. In a programmed system having a memory, a method for conducting an electrophysiology procedure using one or more catheters at least one of which is a roving catheter which includes: one or more first means supported on the catheter for obtaining physiologic data; and one or more second means for obtaining location data concerning a location of the first means when the catheter is positioned indwelling, the method comprising the steps of:
    a) displaying the location data obtained by the second means in a first window;
    b) displaying the physiologic data obtained by the first means in a second window;
    c) freezing the first and second windows to a first moment in time during the electrophysiology procedure in response to operator action;
    d) disassociating in the memory of the programmed system any physiologic data from location data for any moment in time other than the first moment in time; and
    e) creating a set of data points for display in the first window, each data point associating the physiologic data obtained by each first means at the first moment in time with the location data obtained by the second means at the first moment in time.

2. The method of claim 1, wherein the first window and the second window are active panes presented on a single display.

3. In a programmed system, a method for managing discrete data capture requests received throughout the course of an electrophysiology procedure, comprising the steps of:
    a) obtaining physiologic data from sites adjacent one or more locations of a roving catheter distal tip portion;
    b) obtaining location data concerning a location of each of said sites;
    c) providing an index value in response to a request, at any given point in time, to capture the data obtained from steps (a) and (b);
    d) associating in a first memory the obtained physiologic data with the index value;
    e) associating in a second memory the obtained location data with the index value; and
    f) updating the index value prior to repeating steps (c) through (e).

4. The method of claim 3, including the further step of creating a set of data points, the data points associating the physiologic data in the first memory with the location data in the second memory for any one of said any given point in time.

5. The method of claim 4, including the further step of displaying the set of data points in a first window.

6. The method of claim 5, including the further step of displaying in the first window a map of the locations visited during the course of the electrophysiology procedure using the obtained location data for a plurality of index values.

7. In a programmed system, a method for managing discrete data capture requests received throughout the course of an electrophysiology procedure, comprising the steps of:
    a) obtaining physiologic data from sites adjacent one or more locations of a roving catheter distal tip portion;
    b) obtaining location data concerning a location of each of said sites;
    c) providing an index value in response to a request, at any given point in time, to capture the data obtained from steps (a) and (b);

d) associating in a first memory the obtained physiologic data with the index value;
e) associating in a second memory the obtained location data with the index value;
f) updating the index value prior to repeating steps (c) through (e); and
g) displaying in a first window a map of the locations visited during the course of the electrophysiology procedure using the obtained location data for a plurality of index values.

8. The method of claim 7, including the further steps of:
creating a set of data points for display in the first window, the data points associating the physiologic data stored in the first memory with the location data stored in the second memory for any one of said any given points in time; and
displaying the set of data points in the first window.

9. The method of claim 8, including the additional step, prior to the creating step, of retrieving one of the physiologic data from the first memory and the location data from the second memory using the index value, whereby the set of data points displayed in the first window includes physiologic data that was captured at one particular point in time during the course of the electrophysiology procedure.

10. The method of claim 9, wherein the association of the physiologic data stored in the first memory with the location data stored in the second memory for any one of said any given points in time is made in a memory segment, the method including the additional step, prior to the retrieving step of:
disassociating the physiologic data from the location data in the memory segment.

11. The method of claim 9, wherein the index value used to retrieve the physiologic data is selected by the user.

12. The method of claim 11, wherein the first window comprises one or more panes, each having a user-selectable tab to activate a given pane and wherein the index value is selected using the user-selectable tab.

13. The method of claim 11, including the additional step of permitting the user to select from the map a location that was visited, wherein the retrieving step retrieves the physiologic data from the first memory using the index value associated with the selected location.

14. The method of claim 13, including the additional steps of:
permitting the user to select from the map a set of locations that were visited; and
storing the set of locations,
wherein the retrieving step sequentially retrieves the physiologic data for each selected location in the set of locations.

15. The method of claim 14, wherein the sequentially retrieval is in the order that the locations were selected.

16. The method of claim 14, wherein the retrieving step loops through the locations until interrupted.

17. The method of claim 14, wherein the retrieving step has a speed and wherein the speed that data points are displayed for said any given points in time is adjustable.

18. The method of claim 9, wherein the index value used to retrieve the physiologic data is selected by a program executing in the programmed system.

19. In a programmed system, a method for managing discrete data capture requests received throughout the course of an electrophysiology procedure, comprising the steps of:
a) in response to a user request to capture data at any given point in time during the course of the electrophysiology procedure,
    i) associating in a first memory an index value with physiologic data obtained from sites adjacent one or more locations of a catheter distal tip portion at the given point in time; and
    ii) associating in a second memory the index value with location data obtained concerning a location of each of said sites at the given point in time;
b) utilizing the index value to associate in a memory segment of the programmed system the physiologic data in the first memory with the location data in the second memory;
c) creating a set of data points for display in a first window using the information in the memory segment;
d) displaying the set of data points in the first window; and
e) disassociating the physiologic data from the location data in the memory segment for any index value other than the utilized index value;
    whereby the set of data points displayed in the first window show physiologic data for only one particular point in time during the course of the electrophysiology procedure at any moment.

20. The method of claim 19, wherein the index value of the utilizing step is selected by a program executing in the programmed system.

21. A method for discretizing the display of independent data capture events that occur during the course of an electrophysiology procedure, comprising the steps of:
a) utilizing an index value to associate in a memory segment of the programmed system physiologic data in a first memory with location data in a second memory;
b) creating a set of data points for display in a first window using the information in the memory segment;
c) displaying the set of data points in the first window; and
d) disassociating the physiologic data from the location data in the memory segment for any index value other than the utilized index value;
    whereby the set of data points displayed in the first window show physiologic data for only one particular point in time during the course of the electrophysiology procedure at any moment.

22. The method of claim 19 or 21, wherein the index value is selected by the user.

23. The method of claim 22, wherein the first window comprises one or more panes, each having a user-selectable tab to activate a given pane and wherein the index value is selected using the user-selectable tab.

24. The method of claim 19 or 21, wherein the first window further displays a map of the locations visited during the course of the electrophysiology procedure for a plurality of index values.

25. The method of claim 24, including the additional step of permitting the user to select from the map a location that was visited, the selecting step causing the index value associated with the selected location to be utilized in steps (a) through (d).

26. The method of claim 25, including the additional steps of:
permitting the user to select from the map a set of locations that were visited; and
storing the set of locations,
wherein the selecting step sequentially causes the index value associated with each selected location to be utilized in steps (b) through (d).

27. The method of claim 26, wherein the order that the locations were selected governs the sequential utilization of index values.

28. The method of claim 27, wherein the sequential utilization of index values has a speed and wherein the speed that data points are displayed for said any given points in time is adjustable.

29. The method of claim 19 or 21, wherein the memory segment is part of at least one of the first and second memories.

30. The method of claim 21, wherein the index value of the utilizing step is selected by a program executing in the programmed system.

31. The method of claims 18, 20 or 30, wherein the program executing in the programmed system includes the step of automatically selecting physiologic data to be retrieved in accordance with at least one predetermined criterion.

32. The method of claim 31, wherein the at least one predetermined criterion is an earliest activation time.

33. The method of claim 31, wherein the program executing in the programmed system includes the additional steps of sorting the physiologic data to be retrieved in accordance using one of said at least one predetermined criterion, and selecting the physiologic data after the sorting step.

34. The method of claim 31, wherein the program executing in the programmed system includes the additional steps of defining a subset of the physiologic data to be retrieved in accordance using one of said at least one predetermined criterion, and selecting the physiologic data after the defining step.

35. The method of claims 1, 4, 7, 19 or 21, wherein the first window comprises one or more panes, each having a user-selectable tab to activate a given pane.

36. The method of claim 35, wherein only one of the panes is active at a time.

37. The method of claim 36, including the additional steps of permitting a user to select which of the panes is to be active.

38. The method of claim 35, wherein each pane has a transparent background permitting other panes to be viewed therethrough.

39. The method of claim 35, wherein only one of the panes is active at a time and wherein the active pane has an opaque background.

40. The method of claim 39, wherein the active pane is displayed in the foreground of the first window thereby precluding other panes from being viewed.

41. The method of claims 1, 5, 7, 19 or 21, wherein the physiologic data undergoes processing prior to being displayed.

42. The method of claims 3, 7, 19 or 21, wherein the index value is one of a snapshot number and a time stamp.

43. The method of claims 4, 8, 19 or 21 wherein the step of creating a set of data points comprises populating a physiologic data property of a displayable software object with physiologic data from the first memory.

* * * * *